US00PP25636P3

(12) United States Plant Patent
Telch

(10) Patent No.: US PP25,636 P3
(45) Date of Patent: Jun. 23, 2015

(54) RASPBERRY PLANT NAMED 'LAGORAI PLUS'

(50) Latin Name: *Rubus idaeus* L
Varietal Denomination: Lagorai Plus

(71) Applicant: SANT'ORSOLA SOCIETÁ COOPERATIVA AGRICOLA, Pergine Valsugana (IT)

(72) Inventor: Aldo Telch, Faver (IT)

(73) Assignee: SANT' ORSOLA SOCIETA' COOPERATIVA AGRICOLA, Pergine Valsugana (IT)

( * ) Notice: Subject to any disclaimer, the term of this patent is extended or adjusted under 35 U.S.C. 154(b) by 90 days.

(21) Appl. No.: 13/815,342

(22) Filed: Feb. 22, 2013

(65) Prior Publication Data

US 2013/0318664 P1 Nov. 28, 2013

(30) Foreign Application Priority Data

May 25, 2012 (IT) ..... PBR 201200708

(51) Int. Cl.
*A01H 5/08* (2006.01)

(52) U.S. Cl.
USPC ..... Plt./204
CPC ..... *A01H 5/0887* (2013.01)

(58) Field of Classification Search
USPC ..... Plt./204
CPC ..... A01H 5/0887; A01H 5/08; A01H 5/0831
See application file for complete search history.

(56) References Cited

PUBLICATIONS

Moore et al. Raspberry. Register of New Fruit and Nut Cultivars List 46, Hortscience vol. 47(5) May 2012, pp. 536 and 555-556.*

* cited by examiner

*Primary Examiner* — June Hwu
(74) *Attorney, Agent, or Firm* — Ohlandt Greeley Ruggiero & Perle L.L.P.

(57) ABSTRACT

The new raspberry variety 'Lagorai Plus' was obtained by open pollination of hybrid raspberry plant Tulameen at Faver (Cembra Valley, Province of Trento, Region of Trentino, Italy). The new plant is a primocane variety producing two crops per year, wherein the fruits ripen on current season's cane in late autumn and on previous season's cane in mid-summer. The production of autumn is negligible when in summer is very high. The resulting fruits are conical and strong red in coloration.

3 Drawing Sheets

Genus and species: *Rubus idaeus* L.
Variety denomination: 'Lagorai Plus'.

BACKGROUND OF THE NEW VARIETY

A new and distinct red raspberry plant (botanically known as *Rubus idaeus* L.) hereinafter referred to by the name 'Lagorai Plus' is disclosed. The new variety 'Lagorai Plus' was obtained by free pollination of Tulameen individual raspberry plants.

The crossing for the new plant was created in 2003 at Faver (Cembra Valley, Province of Trento, Region Trentino, Italy) and it has been subject to selection on year 2005 and then asexually reproduced repeatedly by root cutting since introduction in 2007. The characteristics of the new plant have been found stable and have been transmitted without change through succeeding (more than 6) asexual propagations.

SUMMARY OF THE INVENTION

The most outstanding and distinguishing characteristics of the 'Lagorai Plus' plant are hereunder reported.

Primocane raspberry plant, but is more interesting growing the variety as floricane;
Good fruit colour and flavour;
Large and firm berries;
Good tolerance to pests and diseases.

The new plant can be propagated by: the use of suckers produced in a spawn-bed, root cutting and use of tissue culture techniques. The root cutting is to be preferred.

BRIEF DESCRIPTION OF THE PHOTOGRAPHS

The new red raspberry plant 'Lagorai Plus' is illustrated by the accompanying photographs showing typical specimens of the new variety in colour as true as reasonably possible to make the same colour illustration of this character by conventional photographic procedures. The photographs are of plants that are two years old.

DETAILED DESCRIPTION

Figure 1:
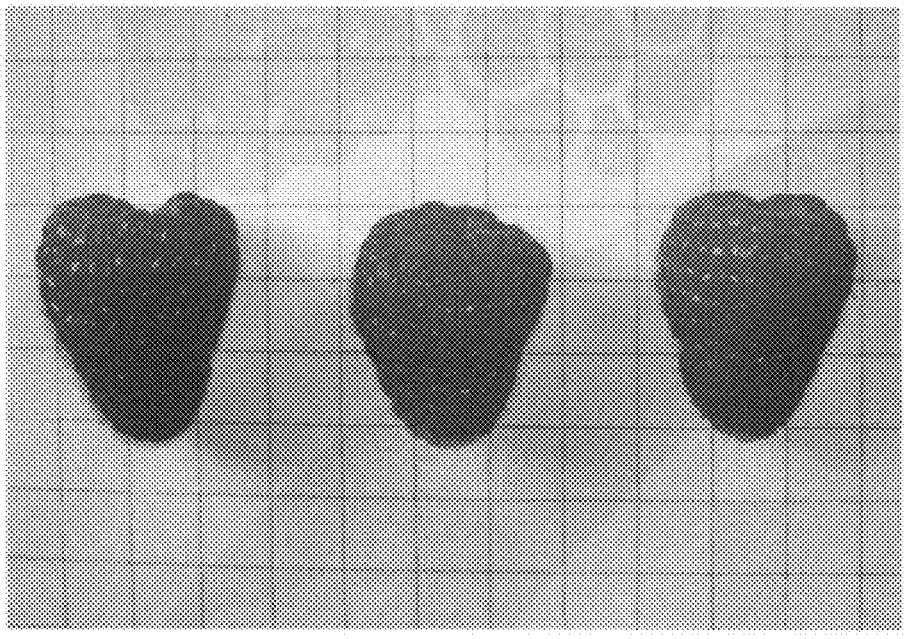
FIG. 1 shows the fruit size, shape and colour at ripening.
Figure 2:
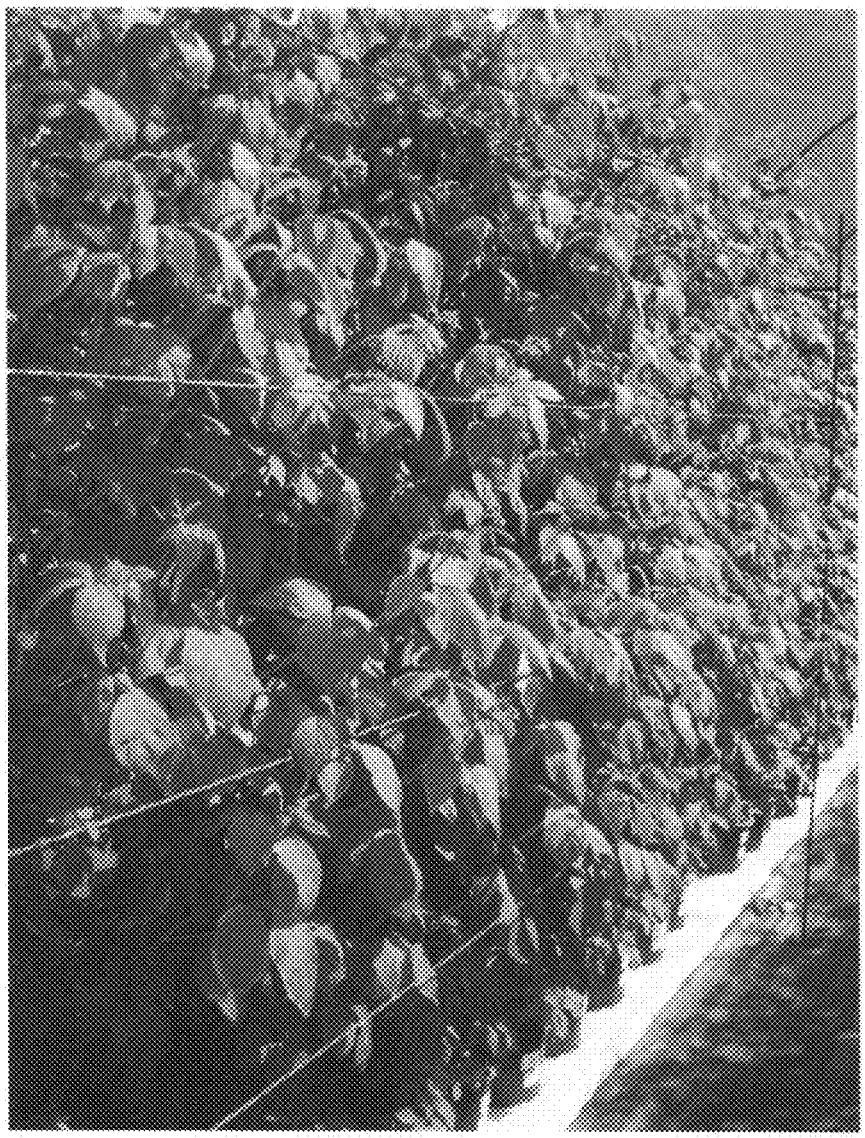
FIG. 2 is a view of raspberry plants showing, in particular, typical distribution of fruit.
Figure 3:
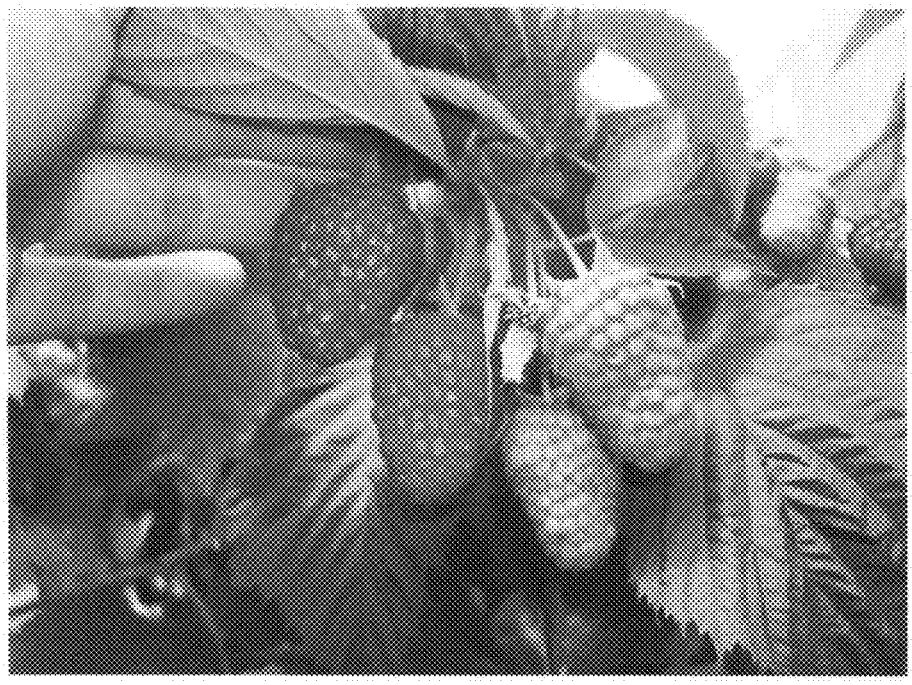
FIG. 3 shows both the ripe and immature fruit size, shape and leaf morphology.

The following detailed description set forth the distinctive characteristics of the new variety 'Lagorai Plus'. The performance of the new plant for retention of its distinctive characteristics has been evaluated through successive asexual propagations by root cutting in the Applicant's setting at Vigolo Vattaro (Province of Trento, Region Trentino, Italy) under controlled conditions of temperature (minimal temperature 15° C. and maximal temperature 28° C.) in greenhouse. The growing was the out of soil using peat as substrate.

The canes have general upright habit and very strong vigour, and require support; the new variety is adapted to medium-high winter chill conditions, such as northern Italy, and has very good root system.

The plant 'Lagorai Plus' is a primocane variety with a very low autumn production, while highly productive in summer. Therefore the variety is grown as floricane.

The plant assessment was performed for 3 years.

Colour references are primarily to The R.H.S. Colour Chart of The Royal Horticultural Society of London (Ed. 2007).

DETAILED BOTANICAL DESCRIPTION

Classification:
- *Family*.—Rosaceae.
- *Botanical*.—*Rubus idaeus* L.
- *Common name*.—Raspberry.

Parentage: Open pollination of Tulameen raspberry plants (female parentage).

Plant:
- *Propagation*.—Root cutting.
- *Height* (*average*).—1.75 m.
- *Spread* (*average*).—0.80 m.

Primocane:
- *Cane colour*.—Greyish Yellowish Green (RHS 194A).
- *Length*.—1.75 m.
- *Diameter*.—13 mm.
- *Texture*.—Hard to very hard.
- *Internode length*.—Medium.
- *Number of current season's shoots*.—Many to very many (40-50 average).
- *Very young shoot*.—Strong Reddish Purple (RHS 72A) of apex during rapid growth present.
- *Dormant cane colour*.—Moderate Brown (RHS 165A).

Floricane:
- *Cane colour*.—Moderate Brown (RHS 165A).
- *Length*.—1.75 m.
- *Diameter*.—13 mm (average).
- *Cane texture*.—Hard to very hard.
- *Internode length*.—Medium.

Spines:
- *Number*.—Calculated on linear shoot extension 1 per cm (average).
- *Shape*.—Triangle.
- *Length*.—3.5-4 mm.
- *Width*.—0.5-1 mm.
- *Apex*.—Pointed.
- *Colour*.—Dark Yellowish Pink (RHS 181D).

Leaves:
- *Type*.—Compound; odd-pinnate and subdivided in 3-7 ovate and serrate small leaves.
- *Position on the lateral leaflets*.—Speculate.
- *Leaf and terminal leaflet length*.—80-110 mm.
- *Leaf and terminal leaflet width*.—90 mm.
- *Shape*.—The leaf apex shape is bluntish to pointed and the leaf base shape is orbicular ovate.
- *Colour*.—Strong Yellowish Green (RHS 134B) on the upper surface and Light Yellowish Green (134D) on the lower surface.
- *Petiole*.—Length (average) 15-20 mm; diameter (average) 3 mm; colour brilliant Yellowish Green (RHS 134C).
- *Texture*.—The superior surface texture is medium hard; the lower surface texture is medium hard.

Stipule:
- *Number per leaf*.—1.
- *Shape*.—Rectangular.
- *Size*.—Length: 4 mm; width: 2 mm.
- *Colour*.—Brilliant Yellowish Green (RHS 134C).

Flowers:
- *Type*.—Inflorescence.
- *Fragrance*.—Absent.
- *Colour*.—Primary colour Greenish White (RHS 155C).
- *Length*.—14-15 mm.
- *Diameter*.—14-15 mm.
- *Shape*.—Racemose.
- *Bloom*.—The blooming begins in the medium-late season, late May and late August.

Petals:
- *Size*.—Length: 5 mm; width: 2.5 mm.
- *Shape*.—Drop shaped.
- *Apex*.—Rounded.
- *Base*.—Bluntish to pointed.
- *Margin*.—Smooth.
- *Texture*.—Thin.
- *Colour*.—Greenish White (RHS 155C).

Buds:
- *Size*.—Length: 8 mm; width: 3.5-4 mm.
- *Diameter*.—3.5-4 mm.
- *Shape*.—Drop shaped.
- *Colour*.—Light Greyish Olive (RHS 195A).

Sepals:
- *Size*.—Length: 7 mm; width: 5 mm.
- *Margin*.—Smooth.
- *Shape*.—The apex is pointed and the base is flat.
- *Texture*.—Thin.
- *Colour*.—Pale Yellowish Green (RHS 193C).

Reproductive organs:
- *Pistils per flower*.—Number: 70-80 (average). Size: length: 10 mm; width 1 mm. Colour: Greenish White (RHS 157D).
- *Stamen*.—Number: 70-80 (average). Size: length: 9 mm; width: 1 mm. Colour: Greenish White (RHS 157D).
- *Ovary*.—Shape: Oval.
- *Filament*.—Colour: Greenish White (RHS 157D).
- *Anther*.—Colour: Moderate Orangish Yellow (RHS 164C).
- *Pollen*.—Colour: Greenish White (RHS 157D).

Fruit:
- *Predominant shape*.—Conical.
- *Weight* (*average*).—6.8 g.
- *Size*.—Length (average) 3.50 cm; width (average) 2.50 cm.
- *Colour of ripe fruit*.—Strong Red (RHS 39A).
- *Main bearing time*.—Both on previous year's cane in summer, mid-June, and on current year's cane in autumn, mid-October.
- *Time of beginning the fruit ripening on previous season's cane*.—Early July.
- *Time of beginning the fruit ripening on current season's cane*.—Late September/early October.
- *Firmness* (*newtons/mm*).—0.20 Kg/inch.
- *Number of drupelets per fruit* (*average*).—30-40.
- *Size of drupelets*.—Medium.
- *Glossiness*.—Large.
- *Adherence to plug*.—Medium.

*Yield* (*average*).—1.3 kg/plant.

*Storage capacity*.—Good shelf-life high yields of good quality fruit sutiable for fresh retailing, good adaptability to frozen retailing.

Pest and disease resistance: Very strong canes, resistance to pests such as *Amphorophora idaei* and diseases such as antrachnose, botrytis, and powdery mildew; the plant needs few spray treatments for disease and pest control.

Comparison with Commercial Plants

'Lagorai Plus' differs from the commercial variety 'Glen Moy' in that 'Lagorai Plus' is as vigorous plant with strong red firm fruit that ripens from late September to early November and allows a late harvest, while 'Glen Moy' is a medium vigorous plant with deep yellowish pink fruit that ripens from mid-September to late October.

The new plant 'Lagorai Plus' is similar to the commercial variety 'Glen Moy'; however, there are several differences as shown in Table 1.

Table 1. Comparison between 'Lagorai Plus', 'Glen Moy' and 'Tulameen'

TABLE 1

Comparison between 'Lagorai Plus', 'Glen Moy' and 'Tulameen'

| Characteristic | 'Lagorai Plus' | 'Glen Moy' | 'Tulameen' |
|---|---|---|---|
| Plant | Vigorous | Medium vigour | Medium vigour |
| Spines | Present | Absent | |
| Fruit | Firmer; late harvest | Medium firmness; early harvest | |
| Fruit ripening time on the current season's cane | Early to Mid-June and Late-September-Early November | Mid-September-Late October | Early to Mid-June |
| Fruit color | Strong Red (RHS 39A) | Deep Yellowish Pink (RHS 44D) | Medium Red |
| Cane color | Medium Brown (RHS 165A) | | Green/brown |
| Roots | Very strong | | Medium strong |

What is claimed is:

1. A new and distinct raspberry plant as substantially herein shown and described.

* * * * *